United States Patent
Stinson et al.

(10) Patent No.: US 9,445,608 B2
(45) Date of Patent: Sep. 20, 2016

(54) ANTIMICROBIAL POWDERS FOR THE PREPARATION OF BAKERY PRODUCTS

(75) Inventors: Jesse Stinson, Lenexa, KS (US); GuoHua Feng, Overland Park, KS (US)

(73) Assignee: Caravan Ingredients Inc., Lenexa, KS (US)

(*) Notice: Subject to any disclaimer, the term of this patent is extended or adjusted under 35 U.S.C. 154(b) by 366 days.

(21) Appl. No.: 13/077,293

(22) Filed: Mar. 31, 2011

(65) Prior Publication Data

US 2012/0251662 A1    Oct. 4, 2012

(51) Int. Cl.

| | |
|---|---|
| A21D 13/00 | (2006.01) |
| A21D 2/14 | (2006.01) |
| A21D 6/00 | (2006.01) |
| A21D 8/04 | (2006.01) |
| A01N 25/08 | (2006.01) |
| A01N 25/12 | (2006.01) |

(52) U.S. Cl.
CPC ........... *A21D 13/0006* (2013.01); *A01N 25/08* (2013.01); *A01N 25/12* (2013.01); *A21D 2/145* (2013.01); *A21D 6/00* (2013.01); *A21D 8/042* (2013.01)

(58) Field of Classification Search
CPC ...... A21D 8/02; A21D 6/00; A21D 13/0006; A21D 13/0061
USPC ......................................................... 426/321
See application file for complete search history.

(56) References Cited

U.S. PATENT DOCUMENTS

| | | |
|---|---|---|
| 3,021,219 A | 2/1962 | Melnick |
| 3,317,323 A | 5/1967 | Lawrence |
| 3,996,386 A | 12/1976 | Malkki et al. |
| 4,407,839 A | 10/1983 | Corbeil et al. |
| 5,225,222 A | 7/1993 | Cha et al. |
| 6,312,741 B1 | 11/2001 | Navarro |
| 6,635,289 B2 | 10/2003 | Horn |
| 7,575,769 B2 | 8/2009 | de Levita et al. |
| 2004/0208963 A1 | 10/2004 | Ueno et al. |
| 2005/0136166 A1 | 6/2005 | de Levita et al. |
| 2005/0191397 A1 | 9/2005 | Williams et al. |
| 2006/0134285 A1 | 6/2006 | Schnieber et al. |
| 2006/0286213 A1 | 12/2006 | de Levita et al. |
| 2007/0065547 A1 | 3/2007 | Coyne et al. |

(Continued)

FOREIGN PATENT DOCUMENTS

| | | |
|---|---|---|
| CN | 1676002 A | 10/2005 |
| EP | 0 009 988 | 4/1980 |

(Continued)

OTHER PUBLICATIONS

Cooking Light "Cinnamon-Bun Bread," Jan. 1999, p. 1-2.*

(Continued)

*Primary Examiner* — Elizabeth Gwartney
(74) *Attorney, Agent, or Firm* — Hovey Williams LLP

(57) ABSTRACT

The present invention is directed to methods and compositions for making dough-based bakery foods, such as bread having extended mold-free shelf-lives, using new antimicrobial powders comprising an antimicrobial agent dispersed in a carrier. The invention is also directed to methods and compositions for preparing dough-based bakery products, such as bread, having long mold-free shelf-lives, by treating the surface of the dough with the antimicrobial powder. Further, the invention is concerned with bakery products having long, mold-free and anti-staling shelf-lives.

17 Claims, 7 Drawing Sheets

(56) References Cited

U.S. PATENT DOCUMENTS

2009/0136636 A1* 5/2009 de Levita et al. ............ 426/310
2009/0204552 A1 8/2009 de Levita et al.
2009/0214732 A1 8/2009 de Levita et al.

FOREIGN PATENT DOCUMENTS

| EP | 1 382 261 | | 1/2004 |
|---|---|---|---|
| WO | WO 2005/032259 | * | 4/2005 |
| WO | 2008110531 | | 9/2008 |
| WO | 2011/156010 | | 12/2011 |

OTHER PUBLICATIONS

The Idea Room—"Cinnamon Swirl Bread," Jan. 5, 2011, http://www.theidearoom.net/2011/01/cinnamon-swirl-bread.html.*
International Search Report and Written Opinion dated Oct. 29, 2012 in corresponding application PCT/US2012/030844 filed on Mar. 28, 2012.
CN1676002A English Abstract, 1 page.
Mingsheng et al., "Food Microbiology," China Light Industry Press, Sep. 30, 2006, pp. 321-322; No English version available.
Yao et al., "Separation, identification and inhibition of spoilage moulds in bakery products," Science and Technology of Food Industry, 2008, 29(11), 148-151. (Abstract only in English).

* cited by examiner

ANTIMICROBIAL POWDERS FOR THE PREPARATION OF BAKERY PRODUCTS

BACKGROUND OF THE INVENTION

1. Field of the Invention

The present invention relates to novel bakery products having long shelf-lives and superior mold growth inhibition. The invention is also directed towards novel methods of making such bakery products using inventive antimicrobial powders ("AMPs"). Furthermore, these properties can be achieved even without the use of chemical preservatives in the doughs themselves.

2. Description of Related Art

The growth of microorganisms, such as mold, rope, spoilage yeast, and bacteria is often the limiting factor in the shelf life of foods. This is especially true for bakery products, such as bread, due to their relatively higher moisture content, higher pH, and the exposure to open air during cooling. The microbial growth not only shortens the shelf-life of bakery products, but also results in difficulties in production, storage and distribution, and sales. A significant amount of such food is wasted either in the store or in consumers' homes due to the microbial growth. Among the problems associated with the shelf-life of bakery products, mold growth has probably become the most critical limiting factor that will determine the shelf-life of future bakery products.

Various methods and preservatives are used in the food industry to inhibit the microbial growth in bakery products. The preservatives commonly used in bakery products are often chemical based, such as calcium propionate, potassium sorbate, etc. However, these chemical preservatives inhibit yeast fermentation, impart an off-flavor to the finished product, and increase the formula and production cost when added to the dough. A number of solutions have been developed to minimize the negative impact of using the above-mentioned chemical preservatives. These include topical spraying of sorbate solution or using encapsulated sorbic acid or propionate that only release the mold inhibitors during the baking stage. Natural preservatives, such as vinegar, raisin juice concentrate, and fermented sugars, etc. are used for mold inhibition in all-natural bakery products. However, these preservatives not only have limited effectiveness in mold inhibition, but also inhibit yeast fermentation, affect the flavor and taste of the final products, and are often much more expensive to use.

There is still a need for improved methods and compositions for inhibiting microbial growth on dough-based products.

SUMMARY OF THE INVENTION

The present invention is broadly concerned with an antimicrobial powder ("AMP") comprising an antimicrobial agent dispersed in a carrier, wherein the powder is substantially salt-free.

The invention is also directed towards a method of extending the shelf-life of a dough-based product. The method comprises treating the surface of a dough with an antimicrobial powder and baking the dough to yield a baked product having an extended mold-free shelf-life. The antimicrobial powder comprises an antimicrobial agent dispersed in a carrier and comprises less than 2% by weight salt, based upon the total weight of the powder taken as 100% by weight.

The invention is also concerned generally with the combination of a food product having an outer surface and a coating of antimicrobial powder adjacent the food product's outer surface. The antimicrobial powder comprises an antimicrobial agent dispersed in a carrier, and comprises less than 2% by weight salt, based upon the total weight of the powder taken as 100% by weight.

A further antimicrobial powder comprising an antimicrobial agent dispersed in a carrier is also provided. The antimicrobial agent is selected from the group consisting of sorbic acid, natamycin, fumaric acid, citric acid, polylysine, sodium benzoate, cinnamon, fermented carbohydrates, and combinations thereof.

The invention is also directed generally towards an antimicrobial powder comprising an antimicrobial agent dispersed in a carrier. The antimicrobial powder is free of calcium propionate, sodium propionate, potassium sorbate, sodium diacetate, ascorbic acid, and propionic acid.

A further method of extending the shelf-life of a dough-based product is also provided. The method comprises shaping a dough, treating the surface of a dough with an antimicrobial powder to yield a treated dough, proofing the treated dough, and baking the treated dough to yield a baked product having an extended mold-free shelf-life. The antimicrobial powder comprises an antimicrobial agent dispersed in a carrier.

DETAILED DESCRIPTION

Figure 1:
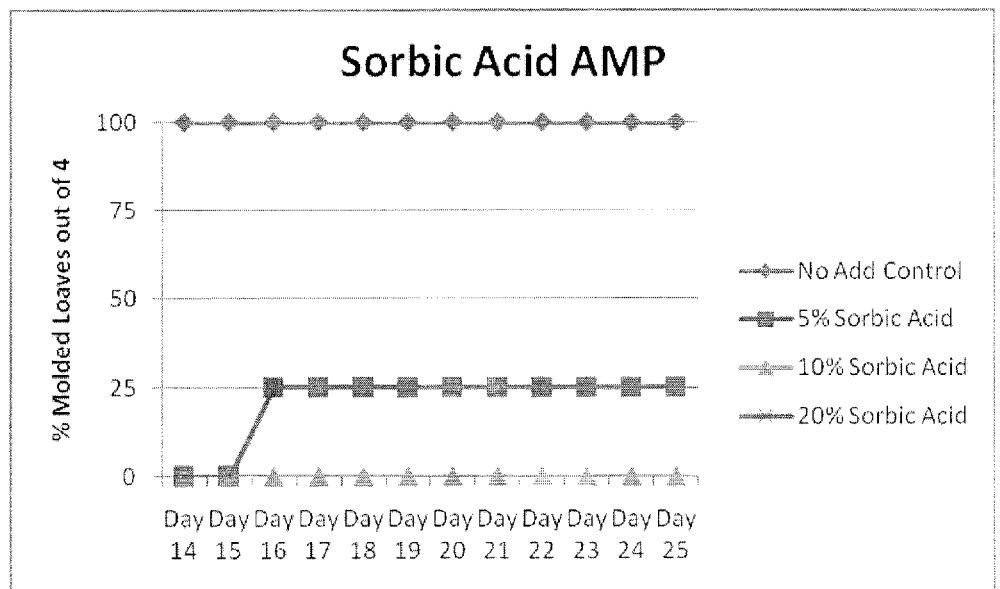
FIG. 1 is a graph of the results from the sorbic acid antimicrobial powder mold inhibition tests from Example 1.

In more detail, the present invention is concerned with novel antimicrobial powders as well as novel methods of making leavened (yeast or chemical) bakery products and other dough-based bakery products having increased mold-free shelf-lives, with yeast-raised products being particularly preferred. These dough-based products include those selected from the group consisting of breads, buns, rolls, bagels, and sandwich thins.

In one method of the invention, the surface of a dough is coated with a novel, antimicrobial powder in accordance with the invention, which can be used in addition to, or in lieu of chemical and/or natural preservatives in the dough formulations themselves. Dusting powders or flours are commonly used in the baking arts as a dry lubricant and are applied to baking equipment and surfaces to prevent sticking of dough and facilitate release of the product during processing. Unlike conventional powders or flours, the inventive antimicrobial powder comprises an antimicrobial agent dispersed in a carrier. The antimicrobial agent and carrier are preferably each provided in powder form. The term "powder," as used herein with respect to the inventive powder and its respective components refers to a relatively free flowing composition of loose (i.e., discrete) particles, particulates, or granules. More preferably, to enhance the flowability and reduce the tendency to clump, the antimicrobial powder is in the form of a substantially dry powder. The moisture content of the antimicrobial powder is preferably less than about 20% by weight, more preferably less than about 16% by weight, and even more preferably less than about 14% by weight, based upon the total weight of the antimicrobial powder taken as 100% by weight.

Suitable chemical or natural antimicrobial agents for use in the invention include those selected from the group consisting of sorbic acid, natamycin, sodium diacetate, calcium propionate, sodium propionate, potassium sorbate, fumaric acid, citric acid, polylysine, sodium benzoate, cinnamon, cultured whey, fermented carbohydrates, and combinations thereof. In some embodiments, the antimicrobial powder is free of calcium propionate, sodium propionate, potassium sorbate, sodium diacetate, ascorbic acid, and propionic acid. That is, the antimicrobial agent is selected from the group consisting of sorbic acid, natamycin, fumaric acid, citric acid, polylysine, sodium benzoate, cinnamon, fermented carbohydrates, and combinations thereof. In further embodiments, the antimicrobial agent is preferably not only effective at inhibiting mold growth, but also shows no negative impact on product quality, such as crust discoloration or spotting. Thus, particularly preferred antimicrobial agents are selected from the group consisting of sorbic acid, natamycin, sodium diacetate, fumaric acid, and combinations thereof. It will be appreciated that the amount of antimicrobial agent in the antimicrobial powder will vary depending upon the particular agent(s) and combinations used in the antimicrobial powder. Ranges for various suitable antimicrobial agents are provided in Table 1 below.

TABLE 1

Antimicrobial Agents

| Antimicrobial Agent | Broad Range* | Preferred Range* | Most Preferred Range* |
| --- | --- | --- | --- |
| Sorbic Acid | 1%-40% | 5%-20% | 7%-10% |
| Natamycin | 0.1%-10% | 0.5%-5% | 1%-2% |
| Sodium Diacetate | 1%-40% | 5%-30% | 10%-20% |
| Calcium Propionate | 1%-40% | 5%-30% | 10%-20% |
| Sodium Propionate | 1%-40% | 5%-30% | 10%-20% |
| Potassium Sorbate | 1%-40% | 5%-30% | 10%-20% |
| Fumaric Acid | 1%-40% | 5%-30% | 10%-15% |
| Citric Acid | 1%-40% | 5%-30% | 10%-20% |
| Polylysine | 0.5%-40% | 5%-30% | 10%-20% |
| Sodium Benzoate | 1%-40% | 10%-30% | 15%-25% |
| Cinnamon | 1%-40% | 5%-30% | 10%-20% |
| Fermented Carbohydrates | 1%-40% | 5%-30% | 10%-25% |

*Based upon the total weight of the antimicrobial powder taken as 100% by weight.

Although the respective particle sizes of the antimicrobial powder components will vary, the antimicrobial agent preferably has an average particle size that is equal to ±20% of the average particle size of the carrier. The average particle size, as used herein, refers to the average maximum surface-to-surface dimension (e.g., diameter in the case of spherical particles) of all particles in a given sample.

Any food-grade powder material can be used as a carrier. However, particularly preferred carriers are selected from the group consisting of flours (e.g., bread, whole wheat, rice, cake, pastry), calcium sulfate, silica, starches (e.g., corn, potato, wheat), fibers, and combinations thereof. In general, the antimicrobial powder preferably comprises from about 60% to about 99% by weight carrier, more preferably from about 70% to about 95%, and even more preferably from about 80% to about 90% by weight carrier, based upon the total weight of the antimicrobial powder taken as 100% by weight. The ratio of antimicrobial agent to carrier in the antimicrobial powder is preferably from about 1:1.5 to about 1:99, more preferably from about 1:2.3 to about 1:19, and even more preferably from about 1:4 to about 1:9. However, in embodiments where the antimicrobial agent is natamycin, the antimicrobial powder preferably comprises from about 80% to about 99.9% by weight carrier, more preferably from about 90% to about 99%, and even more preferably from about 95% to about 98.5% by weight carrier, based upon the total weight of the antimicrobial powder taken as 100% by weight. Likewise, the ratio of antimicrobial agent to carrier in the powders with natamycin is preferably from about 1:4 to about 1:999, more preferably from about 1:9 to about 1:99, and even more preferably from about 1:19 to about 1:66.

Regardless of the embodiment, the antimicrobial powder is preferably prepared by blending the antimicrobial agent with the carrier until a substantially homogeneous mixture is obtained, and more preferably until the antimicrobial agent is substantially uniformly dispersed in the carrier.

The antimicrobial powder can include a number of optional ingredients dispersed in the carrier along with the antimicrobial agent, such as salt, fats/oils, and combinations thereof. For example, when present, the antimicrobial powder comprises less than 2% by weight salt, more preferably less than 1.8% by weight salt, and even more preferably less than 1.5% by weight salt, based upon the total weight of the antimicrobial powder taken as 100% by weight. As used herein, the term "salt" refers to sodium chloride. However, in some embodiments, it is preferred that the antimicrobial powder consists essentially (or even consists) of the antimicrobial agent dispersed in the carrier. The antimicrobial powder is also preferably substantially salt-free in some embodiments. That is, the antimicrobial powder preferably comprises less than 1% by weight salt, more preferably less than about 0.5% by weight salt, and even more preferably about 0% by weight salt, based upon the total weight of the antimicrobial powder taken as 100% by weight. The antimicrobial powder is also preferably substantially free of corn meal. That is, the antimicrobial powder preferably comprises less than about 1% by weight corn meal, more preferably less than about 0.5% by weight corn meal, and even more preferably about 0% by weight corn meal, based upon the total weight of the antimicrobial powder taken as 100% by weight. The antimicrobial powder is also preferably substantially free of any added fats or oils. That is, the antimicrobial powder preferably comprises less than about 1% by weight fat or oil, more preferably less than about 0.5% by weight fat or oil, and even more preferably about 0% by weight fat or oil, based upon the total weight of the antimicrobial powder taken as 100% by weight. In some embodiments, the antimicrobial powder is also substantially free of any starches (e.g., corn starch). That is, the antimicrobial powder preferably comprises less than about 1% by weight corn starch, more preferably less than about 0.5% by weight corn starch, and even more preferably about 0% by weight corn starch, based upon the total weight of the antimicrobial powder taken as 100% by weight.

The antimicrobial powder is preferably utilized to treat the surfaces of the dough. More specifically, the antimicrobial powder is applied to the surfaces of the dough, preferably after the dough is molded/shaped, but before proofing or baking. Unlike conventional dusting powders, the antimicrobial powders are preferably applied directly to the dough (after shaping/before proofing) rather than being applied to the equipment. The antimicrobial powder is preferably utilized at an amount of from about 0.1% to about 2% by weight, more preferably from about 0.3% to about 1% by weight antimicrobial powder, and even more preferably from about 0.5% to about 0.75% by weight antimicrobial powder, based upon the total weight of the treated dough taken as 100% by weight. In some embodiments, the antimicrobial powder can be applied to the surfaces of the dough that come into contact with the sheets, pans, or other substrates used for baking or holding the dough (i.e., the "contacting" surfaces of the dough), or to those surfaces of the dough that do not come into contact with these substrates, such as the crown of a bread loaf (i.e., the "non-contacting" or "exposed" surfaces of the dough), or a combination thereof. Preferably, the antimicrobial powder coats at least about 25% of the surface area of the dough, more preferably at least about 50% of the surface area of the dough, even more preferably from about 75% to about 80% of the surface area of the dough, and most preferably from about 95% to about 100% of the surface area of the dough, based upon the total surface area of the dough taken as 100%. More preferably, the dough piece is completely (about 100% of the surface area) and uniformly coated with a thin layer of the antimicrobial powder. The antimicrobial powder can be applied to the dough surfaces by any method suitable for coating the exterior surface of the dough, such as sprinkling over the surface of the dough, rolling the dough in the antimicrobial powder, or any combination thereof.

It will be appreciated that any of the foregoing application methods can be carried out alone, or in combination with another suitable method of preventing mold growth. For example, the antimicrobial powder can be applied to the contacting surfaces of the dough as described above, followed by spraying the non-contacting surfaces of the dough with a chemical preservative, such as potassium sorbate, either before or after baking. The treatment of the surface of the dough described herein may also be used in combination with the addition of natural or chemical preservatives inside the dough to maximize the antimicrobial effects and to extend the mold-free shelf-life of the resulting baked product. However, the inventive antimicrobial powder can also be used with doughs formulated without chemical-based preservatives or without any preservatives or other antimicrobial agents at all. Thus, in one aspect of the invention, although the surface of the dough is treated with the antimicrobial powder, the dough formulations themselves preferably comprise less than about 1% by weight preservatives inside the dough formulation, more preferably less than about 0.5% by weight preservatives, and even more preferably are free of any preservatives inside the dough formulation, based upon the total weight of the flour taken as 100% by weight. In this way, the disadvantages of the traditional preservatives in the dough are avoided, while still providing a dough-based product with extended mold-free shelf-life.

Thus, although the antimicrobial effectiveness can be greatly enhanced by the combinations of surface treatments of the dough-based products and the addition of natural or chemical preservatives inside the dough, the present invention is preferably used to reduce or even eliminate the need for preservatives or other antimicrobial agents added inside of the dough. By reducing or eliminating the preservatives inside the dough, the invention can reduce or avoid many problems associated with the preservatives inside the dough, such as yeast inhibition, off-flavors, and other negative impacts on the color and the texture of the final products. Accordingly, in some embodiments, the antimicrobial agent in the antimicrobial powder is the only antimicrobial agent used to extend the shelf-life of the dough-based products. That is, the antimicrobial powder and/or the dough formulations themselves are preferably substantially free of any other antimicrobial agents, and more specifically comprise less than about 2% by weight of other antimicrobial agents, more preferably less than about 1% by weight of other antimicrobial agents, based upon the total weight of the antimicrobial powder or baked product taken as 100% by weight, as applicable. The term "antimicrobial," as used herein, refers to any agent that kills or inhibits the growth of bacteria, fungi, or protozoans. Thus, the term "other antimicrobial agents," as used herein, refers to any other antimicrobial agents besides the specifically enumerated antimicrobial agents in the antimicrobial powder of the invention, as described above.

The inventive antimicrobial powder is suitable for use with any dough-based products. However, in a preferred method of making dough-based products having an extended shelf-life, a plurality of ingredients for the leavened dough-based products are mixed together with flour to form the dough. These ingredients and their preferred ranges are set forth in Table 2.

TABLE 2

Ingredients for Dough-Based Products

| Ingredient | Broad Range* | Preferred* | Most Preferred* |
|---|---|---|---|
| Leavening agent | 0.5%-10% | 2%-8% | 4%-8% |
| Dough Conditioner | 0%-10% | 0.2%-5% | 0.3%-3% |
| Water | 30%-90% | 45%-80% | 50%-70% |
| Non-Fat Dry Milk | 0%-5% | 0.001%-3% | 0.01%-2% |
| Salt | 0%-4% | 1%-3% | 1.5%-2% |
| Sugar | 0%-55% | 4%-20% | 6%-15% |

TABLE 2-continued

Ingredients for Dough-Based Products

| Ingredient | Broad Range* | Preferred* | Most Preferred* |
|---|---|---|---|
| Oil/Fat | 0%-10% | 1%-5% | 2%-3% |
| Mono- and Diglycerides | 0%-5% | 0%-3% | 0.5%-2% |
| Vital Wheat Gluten | 0%-20% | 0%-10% | 0%-5% |
| Enzymes | 0%-5% | 0.1%-1% | 0.2%-46% |
| Preservatives | 0%-2% | 0.1%-1% | 0.2%-0.5% |

*Baker's percentage (100% flour).

The term "baker's percentage," as used herein, refers to the amount by weight of an ingredient in the formulation expressed as a percentage of the total flour weight (which is always 100%). Suitable flours for use in the dough-based formulations include enriched bleached flour, all-purpose flour, whole wheat flour, pastry flour, bread flour, white wheat flour, rye flour, and mixtures thereof.

Suitable leavening agents include yeast, sodium bicarbonate, potassium bicarbonate, sodium aluminum phosphate, sodium acid pyrophosphate, sodium aluminum sulfate, monocalcium phosphate, any other leavening acids, and combinations thereof. Yeast is the preferred leavening agent for the dough formulations and can be any yeast conventionally used in yeast-raised bakery products, with compressed yeast being preferred.

The term "dough conditioner," as used herein, is intended to refer to additives that affect the condition (handling characteristics, machinability) of the dough, as well as those that actually strengthen the dough by increasing its resistance to mechanical stress. Suitable chemical dough conditioners include those selected from the group consisting of sodium stearoyl lactylate (SSL), metabisulfite, calcium stearoyl lactylate (CSL), diacetyl tartaric acid esters of mono-diglycerides (DATEM), ethoxylated monoglycerides, potassium bromate, potassium iodate, azodicarbonamide (ADA), calcium peroxide, potassium sorbate, sorbic acids, and L-cysteine. Suitable natural dough conditioners include those selected from the group consisting of ascorbic acid, enzyme active soy flour, amylases (fungal), xylanases, hemicellulases, proteases, glucose oxidases, hexose oxidases, peroxidases, lipases, phospholipases, transglutaminases, and cellulases. A preferred dough conditioner is sold under the name DEPENDOX® AXC (a blend of ascorbic acid, ADA, fungal enzymes, and wheat starch; available from Caravan Ingredients).

The sugar can be any typical sugar used in bakery products, including granulated brown or white sugar, high fructose corn syrup, corn syrup, fructose, invert sugar, honey, molasses, maple syrup, and mixtures thereof.

The preferred oil or fat is selected from the group consisting of soy oil, partially hydrogenated soy oil, lard, palm oil, corn oil, cottonseed oil, canola oil, vegetable shortening, and mixtures thereof.

The dough compositions can also include anti-staling enzymes, such as amylases. Preferred anti-staling amylases are maltogenic amylases, such as maltogenic α-amylase, G-4 amylase, G+ amylase, and thermally-stable bacterial amylase. Even more preferably, the anti-staling amylase is a maltogenic exoamylase, such as one sold under the name NOVAMYL® 10,000 by Novozymes A/S, as described in U.S. Patent Application Pub. No. 2009/0297659, incorporated by reference herein in its entirety. When present, NOVAMYL® 10,000 is used at activity levels of from about 0.001-40,000 MANU/kg of flour, more preferably from about 5,000 to about 30,000 MANU/kg of flour, and even more preferably from about 5,000 to about 10,000 MANU/ kg of flour. As used herein, one MANU (Maltogenic Amylase Novo Unit) is defined as the amount of enzyme required to release one µmol of maltose per minute at a concentration of 10 mg of maltotriose (Sigma M 8378) substrate per ml of 0.1 M citrate buffer, pH 5.0 at 37° C. for 30 minutes. Use of the maltogenic amylase at these high levels results in many significant advantages, as described in U.S. Patent Application Pub. No. 2009/0297659. For example, utilizing the maltogenic amylase at high levels may allow for the quantity of other ingredients commonly used in the industry to be reduced. That is, the following formula changes might be made: decreased sugar, increased water, decreased yeast, reduced dough conditioners.

The dough formulations can also include other enzymes in addition to, or in lieu of, the anti-staling amylase. Such other enzymes include those selected from the group consisting of asparaginase, lactase, amyloglucosidase, pullulanse, and combinations thereof.

In some embodiments, the dough formulations can also include preservatives. Suitable preservatives for use in the dough formulations include natural and chemical preservatives. Preferred natural preservatives for use in the dough formulations include those selected from the group consisting of vinegar, raisin juice concentrate, fermented whey, fermented flour, fermented starch, fermented or cultured sugars. Preferred chemical-based preservatives for use in the dough formulations include those selected from the group consisting of sorbic acid, potassium sorbate, propionic acid, sorbyl-palmitate, sodium propionate, benzoates, methyl and propyl paraben, calcium propionate. The preservatives can also be used in encapsulated form. When present in the formulations, the dough formulations will include preservatives in an amount of from about 0.1 baker's % to about 2 baker's %, more preferably from about 0.2 baker's % to about 1 baker's %, and most preferably from about 0.3 baker's % to about 0.6 baker's %.

The dough formulations can also include additives such as artificial flavors, spices, colorings, hydrocolloids, and Vital Wheat Gluten.

In forming the dough-based products according to the invention, the ingredients listed in Table 2 above can be simply mixed together in one stage using a "no-time dough process," or they can be subjected to a "sponge and dough process." In the latter process, part of the flour (e.g., 55-75% by weight of the total flour) is mixed with water, yeast, and preferably some of the dough conditioner (if utilized) and allowed to ferment for a time period of from about 3 hours to about 4 hours at from about 70° F. to about 90° F. and from about 80% to about 90% relative humidity. This forms the "sponge." After this time period, the remaining ingredients are mixed with the sponge for a time period of from about 2 minutes to about 20 minutes.

Regardless of the embodiment, the resulting dough is preferably allowed to rest for a time period of from about 5 minutes to about 15 minutes before being divided and formed into the desired size pieces. The dough can then be treated with the antimicrobial powder before being placed in or on a baking pan or other surface. The dough is then preferably allowed to proof at a temperature of from about 95° F. to about 105° F. at a relative humidity of from about 75% to about 95% for a time period of from about 50 minutes to about 70 minutes. The dough can then be baked using the times and temperatures necessary for the type and size of product being made (e.g., from about 400° F. to about 440° F. for about 15 minutes to about 30 minutes). After baking, the resulting baked product is removed from the pan, allowed to cool for about 40 to about 65 minutes, and packaged for distribution or sale.

Bakery products formed according to the present invention have greatly improved mold-free shelf-lives, while also avoiding the many negative effects of adding mold inhibitors in the dough directly, such as inhibiting yeast fermentation or leaving an unpleasant taste in the finished products. More specifically, the resulting baked products will have a mold-free shelf-life of at least about 7 days, more preferably at least about 14 days, and even more preferably at least about 30 days under ambient conditions (~72° F. and 40-75% relative humidity). While the present invention greatly improves mold-free shelf life, it can be used in combination with anti-staling technologies, such as anti-staling enzymes so that the shelf life of those bakery products can be truly maximized. In fact, antimicrobial and anti-staling technologies complement each other, and are preferably used in combination to greater enhance the value of each technology and significantly extend the shelf life of bakery products. As used herein, the term "mold-free" means that there is no mold growth on the surface of the treated food product visible to the naked eye (i.e., unaided by magnification). The significant shelf-life extension of such dough-based products can help increase the production efficiency (by producing large numbers of products in a longer production run and by storing away the product without loss of product quality), to expand the distribution network and market size, and to reduce the waste of the final products both in retail stores and in the consumer's home.

EXAMPLES

The following examples set forth methods in accordance with the invention. It is to be understood, however, that these examples are provided by way of illustration and nothing therein should be taken as a limitation upon the overall scope of the invention.

Example 1

Dough Formulation A

1. Preparation of Dough

In this Example, breads without any chemical preservatives, such as calcium propionate, in the dough were prepared according to the following dough bread making process, using the ingredients in Table 3 below.

TABLE 3

Dough Formulation A

| INGREDIENTS | Bakers % | Grams |
|---|---|---|
| White Bread Flour | 100.00 | 3000 |
| Compressed Yeast | 6.00 | 180 |
| Sodium Stearoyl Lactylate (SSL) | 0.50 | 15 |
| Ice Water | 56.00 | 1680 |
| Non-fat dry milk (NFDM) | 1.00 | 30 |
| Sugar | 8.00 | 240 |
| Dependox ® AXC[A] | 0.04 | 1.2 |
| Soy Oil | 2.00 | 60 |
| Salt | 2.00 | 60 |

[A]A blend of ascorbic acid, azodicarbonamide (ADA), fungal enzymes, and wheat starch (available from Caravan Ingredients).

All of the ingredients except for the salt were added to a 20 qt Hobart mixer, and mixed with a spiral hook on the 1st speed setting (low) for two minutes. The sides of the mixing bowl were scraped, and the ingredients were mixed for 8 minutes at the 2nd speed setting (high). The salt was added, followed by mixing at the 2nd speed setting for an additional 3 minutes until full dough development. The dough was allowed to rest on a wood bench for 10 minutes, and then divided into 535-gram dough pieces, which were then rounded and allowed to rest for an additional 5 minutes. Next, a Gemini Straight Grain Moulder was used, according to the settings in Table 4 below, to sheet and mould the dough pieces.

TABLE 4

| Gemini Straight Grain Moulder Settings | |
|---|---|
| Rollers | 5/3 |
| Pressure Bd. | 32/31 |
| Guide Rails | 16/14 |

The shaped dough pieces were then evenly coated with 2 grams of various antimicrobial powders containing different antimicrobial agents, as described below, and then placed into 1-lb loaf pans. Next, the loaves were proofed at 104° F. and 86% humidity for 1 hour. The loaves were then removed from the proof box and baked at 420° F. for 20 minutes. After baking, the loaves were removed from the oven and depanned. The loaves were cooled on wire racks for 1 hour and then bagged in poly bags with twist ties. The bread was stored at room temperature (~72° F.) to observe mold growth.

2. Antimicrobial Powders

Each of the antimicrobial powders used above was prepared by adding the ingredients in the tables below to a 5 qt Hobart mixer and blending with a paddle attachment for 10 minutes.

A. Sorbic Acid Antimicrobial Powder

| | Grams | | | |
|---|---|---|---|---|
| | 0% | 5% | 10% | 20% |
| Sorbic Acid | 0 | 12.5 | 25 | 50 |
| Wheat Flour | 250 | 237.5 | 225 | 200 |
| Total | 250 | 250 | 250 | 250 |

B. Natamycin Antimicrobial Powder

Two separate tests were performed using Natamycin powder in varying amounts, as indicated below.

| | Grams | | |
|---|---|---|---|
| Test 1 | 0% | 2.5% | 5% |
| Natamycin | 0 | 6.25 | 12.5 |
| Wheat Flour | 250 | 243.75 | 237.5 |
| Total | 250 | 250 | 250 |

| | Grams | | | |
|---|---|---|---|---|
| Test 2 | 0% | .5% | 1.5% | 2.5% |
| Natamycin | 0 | 1.25 | 3.75 | 6.25 |
| Wheat Flour | 250 | 248.75 | 246.25 | 243.75 |
| Total | 250 | 250 | 250 | 250 |

C. Sodium Diacetate Antimicrobial Powder

|  | Grams | | |
| --- | --- | --- | --- |
|  | 0% | 10% | 20% |
| Sodium Diacetate | 0 | 25 | 50 |
| Wheat Flour | 250 | 225 | 200 |
| Total | 250 | 250 | 250 |

D. Potassium Sorbate Antimicrobial Powder

|  | Grams | | | | |
| --- | --- | --- | --- | --- | --- |
|  | 0% | 5% | 10% | 20% | 30% |
| Potassium Sorbate | 0 | 12.5 | 25 | 50 | 75 |
| Wheat Flour | 250 | 237.5 | 225 | 200 | 175 |
| Total | 250 | 250 | 250 | 250 | 250 |

E. Calcium Propionate Antimicrobial Powder

|  | Grams | | | |
| --- | --- | --- | --- | --- |
|  | 0% | 5% | 10% | 20% |
| Calcium Propionate | 0 | 12.5 | 25 | 50 |
| Wheat Flour | 250 | 237.5 | 225 | 200 |
| Total | 250 | 250 | 250 | 250 |

F. Fumaric Acid Antimicrobial Powder

|  | Grams | |
| --- | --- | --- |
|  | 5% | 10% |
| Fumaric Acid | 12.5 | 25 |
| Wheat Flour | 237.5 | 225 |
| Total | 250 | 250 |

G. Fermented Carbohydrate Antimicrobial Powder

|  | Grams | | |
| --- | --- | --- | --- |
|  | 10% | 20% | 30% |
| Caparve[A] | 25 | 50 | 75 |
| Wheat Flour | 225 | 200 | 175 |
| Total | 250 | 250 | 250 |

[A]Inhibit 1400: wheat flour, natural flavor (Mezzoni Foods, Inc.; El Cerrito, CA).

H. Polylysine Antimicrobial Powder

|  | Grams | | | | |
| --- | --- | --- | --- | --- | --- |
|  | 0% | 5% | 10% | 20% | 30% |
| Polylysine | 0 | 12.5 | 25 | 50 | 75 |
| Wheat Flour | 250 | 237.5 | 225 | 200 | 175 |
| Total | 250 | 250 | 250 | 250 | 250 |

I. Cinnamon Powder Antimicrobial Powder

|  | Grams | | |
| --- | --- | --- | --- |
|  | 5% | 10% | 20% |
| Cinnamon Powder | 12.5 | 25 | 50 |
| Wheat Flour | 237.5 | 225 | 200 |
| Total | 250 | 250 | 250 |

J. Sodium Benzoate Antimicrobial Powder

Sodium benzoate antimicrobial powder was prepared according to the same procedure as the other antimicrobial powders, except that in one of the powder formulations a quantity of Fumaric acid was also added to the powder as indicated in the table below.

|  | Grams | | | |
| --- | --- | --- | --- | --- |
|  | 0% | 10% | 20% | 18% |
| Sodium Benzoate | 0 | 25 | 50 | 50 |
| Fumaric Acid | 0 | 0 | 0 | 25 |
| Wheat Flour | 250 | 225 | 200 | 200 |
| Total | 250 | 250 | 250 | 250 |

K. Sodium Propionate Antimicrobial Powder

|  | Grams | | | |
| --- | --- | --- | --- | --- |
|  | 0% | 5% | 10% | 20% |
| Sodium Propionate | 0 | 12.5 | 25 | 50 |
| Wheat Flour | 250 | 237.5 | 225 | 200 |
| Total | 250 | 250 | 250 | 250 |

3. Results

The Results are provided for each antimicrobial powder below.

A. Sorbic Acid Antimicrobial Powder

Sorbic acid antimicrobial powder was effective at mold inhibition and did not impact the appearance of the bread. The results are provided in Table 5 below, as well as in FIG. 1.

TABLE 5

| Sorbic Acid Antimicrobial Powder.* | | | | |
| --- | --- | --- | --- | --- |
| Day | No Add Control | 5% Sorbic Acid | 10% Sorbic Acid | 20% Sorbic Acid |
| 14 | 100 | 0 | 0 | 0 |
| 15 | 100 | 0 | 0 | 0 |
| 16 | 100 | 25 | 0 | 25** |
| 17 | 100 | 25 | 0 | 25 |
| 18 | 100 | 25 | 0 | 25 |
| 19 | 100 | 25 | 0 | 25 |
| 20 | 100 | 25 | 0 | 25 |
| 21 | 100 | 25 | 0 | 25 |
| 22 | 100 | 25 | 0 | 25 |
| 23 | 100 | 25 | 0 | 25 |
| 24 | 100 | 25 | 0 | 25 |
| 25 | 100 | 25 | 0 | 25 |
| 26 | 100 | 25 | 0 | 25 |
| 27 | 100 | 25 | 0 | 25 |
| 28 | 100 | 25 | 0 | 25 |
| 29 | 100 | 25 | 0 | 25 |

*% of molded bread out of 4 loaves (e.g., 50 means two out of four loaves had at least one spot of mold growth).
**On Day 16, the bread with 20% Sorbic Acid only had mold growth on the unprotected break and shred.

B. Natamycin Antimicrobial Powder

Figure 2:
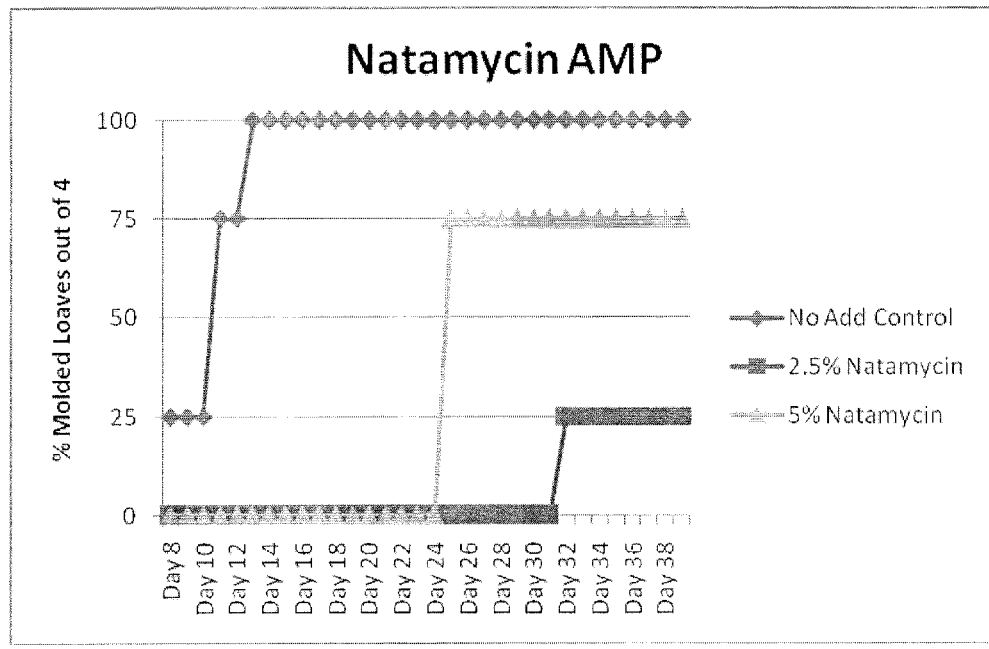
FIG. 2 is a is a graph of the results from mold inhibition test 1 of the natamycin antimicrobial powder from Example 1.

For Test 1, it was found that Natamycin Antimicrobial Powder was effective at mold inhibition and did not impact the appearance of the bread. The results are provided in Table 6 below, as well as in FIG. 2.

TABLE 6

Natamycin Antimicrobial Powder, Test 1*

| Day | No Add Control | 2.5% Natamycin | 5% Natamycin |
|---|---|---|---|
| 8 | 25 | 0 | 0 |
| 9 | 25 | 0 | 0 |
| 10 | 25 | 0 | 0 |
| 11 | 75 | 0 | 0 |
| 12 | 75 | 0 | 0 |
| 13 | 100 | 0 | 0 |
| 14 | 100 | 0 | 0 |
| 15 | 100 | 0 | 0 |
| 16 | 100 | 0 | 0 |
| 17 | 100 | 0 | 0 |
| 18 | 100 | 0 | 0 |
| 19 | 100 | 0 | 0 |
| 20 | 100 | 0 | 0 |
| 21 | 100 | 0 | 0 |
| 22 | 100 | 0 | 0 |
| 23 | 100 | 0 | 0 |
| 24 | 100 | 0 | 0 |
| 25 | 100 | 0 | 75 |
| 26 | 100 | 0 | 75 |
| 27 | 100 | 0 | 75 |
| 28 | 100 | 0 | 75 |
| 29 | 100 | 0 | 75 |
| 30 | 100 | 0 | 75 |
| 31 | 100 | 0 | 75 |
| 32 | 100 | 25 | 75 |
| 33 | 100 | 25 | 75 |
| 34 | 100 | 25 | 75 |
| 35 | 100 | 25 | 75 |
| 36 | 100 | 25 | 75 |
| 37 | 100 | 25 | 75 |
| 38 | 100 | 25 | 75 |
| 39 | 100 | 25 | 75 |

*% of molded bread out of 4 loaves.

Figure 3:
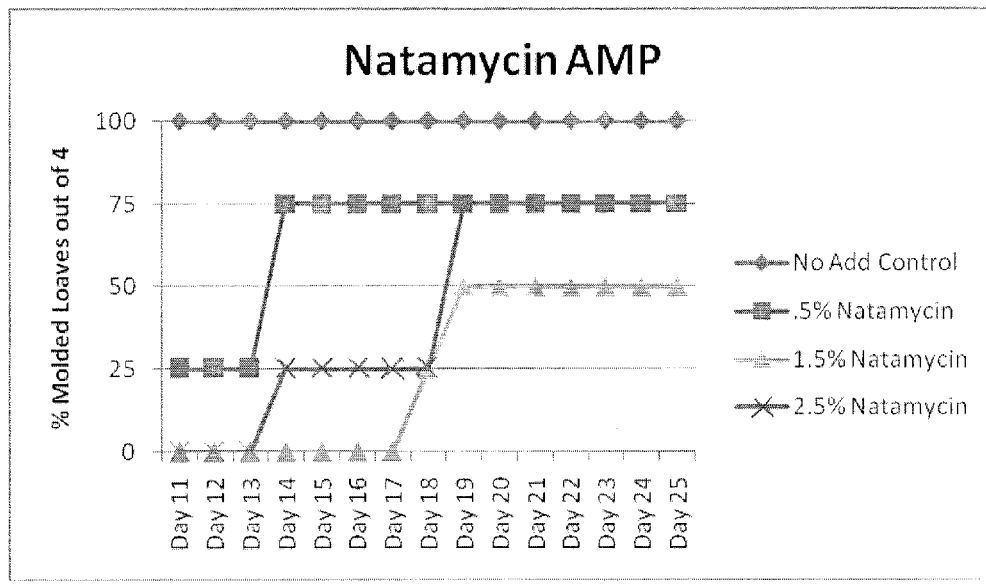
FIG. 3 is a is a graph of the results from mold inhibition test 2 of the natamycin antimicrobial powder from Example 1.

Based upon the results from Test 2, it was found that at least 1.5% by weight Natamycin was required in the powder to obtain mold inhibition. The results for Test 2 are provided in Table 7 below, as well as in FIG. 3.

TABLE 7

Natamycin Antimicrobial Powder, Test 2*

| Day | No Add Control | .5% Natamycin | 1.5% Natamycin | 2.5% Natamycin |
|---|---|---|---|---|
| 11 | 100 | 25 | 0 | 0 |
| 12 | 100 | 25 | 0 | 0 |
| 13 | 100 | 25 | 0 | 0 |
| 14 | 100 | 75 | 0 | 25 |
| 15 | 100 | 75 | 0 | 25 |
| 16 | 100 | 75 | 0 | 25 |
| 17 | 100 | 75 | 0 | 25 |
| 18 | 100 | 75 | 25 | 25 |
| 19 | 100 | 75 | 50 | 75 |
| 20 | 100 | 75 | 50 | 75 |
| 21 | 100 | 75 | 50 | 75 |
| 22 | 100 | 75 | 50 | 75 |
| 23 | 100 | 75 | 50 | 75 |
| 24 | 100 | 75 | 50 | 75 |
| 25 | 100 | 75 | 50 | 75 |

*% molded bread out of 4 loaves.

C. Sodium Diacetate Antimicrobial Powder

Figure 4:
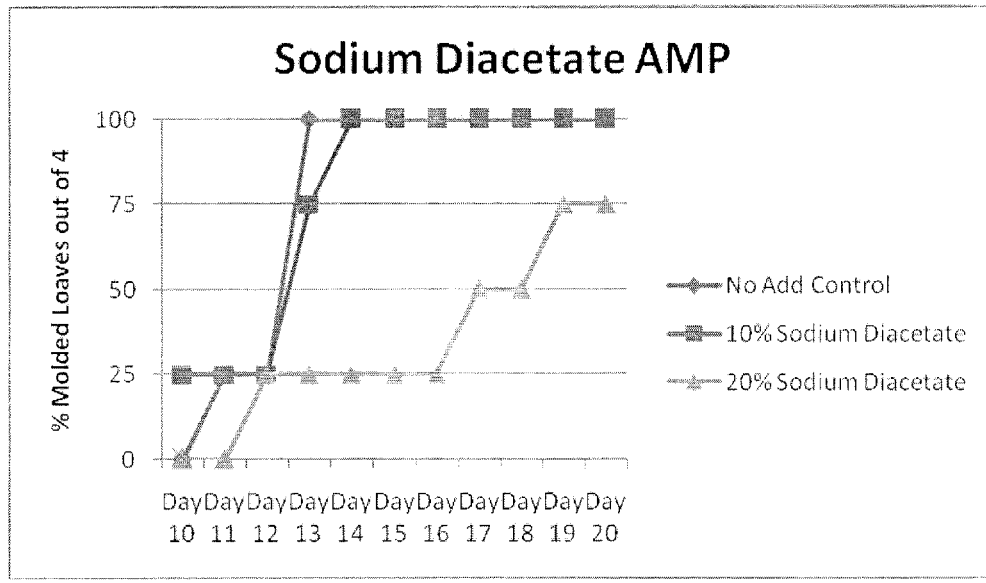
FIG. 4 is a graph of the results from the sodium diacetate antimicrobial powder mold inhibition tests from Example 1.

Sodium Diacetate Antimicrobial Powder was observed to have an effect on mold inhibition at levels of 20% by weight, and it did not impact the appearance of the bread. The results are provided in Table 8 below, as well as in FIG. 4.

TABLE 8

Sodium Diacetate Antimicrobial Powder.*

| Day | No Add Control | 10% Sodium Diacetate | 20% Sodium Diacetate |
|---|---|---|---|
| 10 | 0 | 25 | 0 |
| 11 | 25 | 25 | 0 |
| 12 | 25 | 25 | 25 |
| 13 | 100 | 75 | 25 |
| 14 | 100 | 100 | 25 |
| 15 | 100 | 100 | 25 |
| 16 | 100 | 100 | 25 |
| 17 | 100 | 100 | 50 |
| 18 | 100 | 100 | 50 |
| 19 | 100 | 100 | 75 |
| 20 | 100 | 100 | 75 |
| 21 | 100 | 100 | 75 |

*% molded bread out of 4 loaves.

D. Potassium Sorbate Antimicrobial Powder

Figure 5:
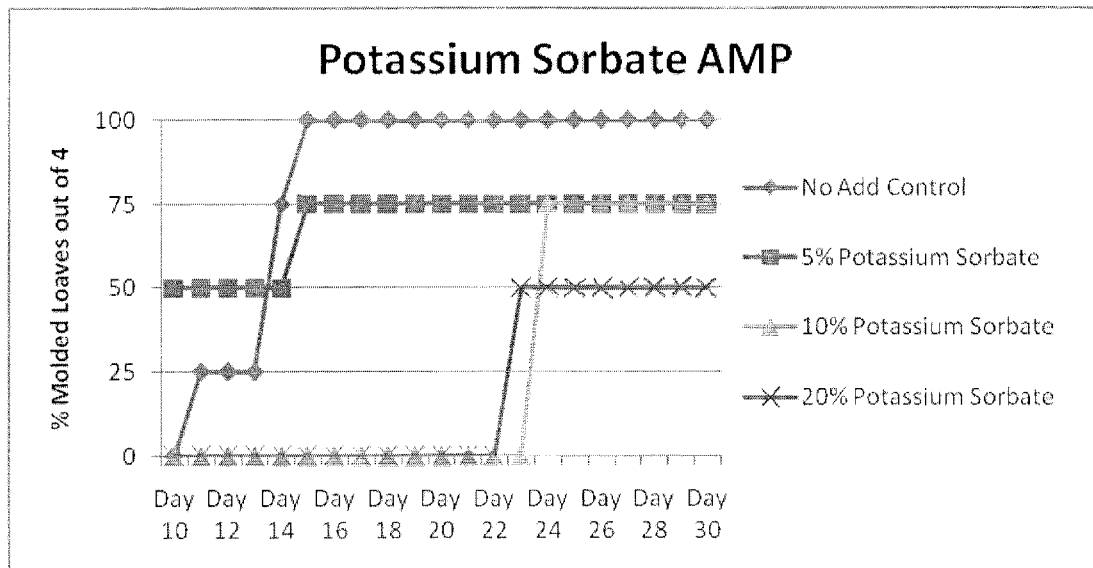
FIG. 5 is a graph of the results from the potassium sorbate antimicrobial powder mold inhibition tests from Example 1.

Potassium Sorbate Antimicrobial Powder was effective at mold inhibition, but negatively impacted the appearance of the bread, as it caused a significant darkening of the crust color. The results are provided in Table 9 below, as well as in FIG. 5.

TABLE 9

Potassium Sorbate Antimicrobial Powder.*

| Day | No Add Control | 5% K Sorbate | 10% K Sorbate | 20% K Sorbate |
|---|---|---|---|---|
| 10 | 0 | 50 | 0 | 0 |
| 11 | 25 | 50 | 0 | 0 |
| 12 | 25 | 50 | 0 | 0 |
| 13 | 25 | 50 | 0 | 0 |
| 14 | 75 | 50 | 0 | 0 |
| 15 | 100 | 75 | 0 | 0 |
| 16 | 100 | 75 | 0 | 0 |
| 17 | 100 | 75 | 0 | 0 |
| 18 | 100 | 75 | 0 | 0 |
| 19 | 100 | 75 | 0 | 0 |
| 20 | 100 | 75 | 0 | 0 |
| 21 | 100 | 75 | 0 | 0 |
| 22 | 100 | 75 | 0 | 0 |
| 23 | 100 | 75 | 0 | 50 |
| 24 | 100 | 75 | 75 | 50 |
| 25 | 100 | 75 | 75 | 50 |
| 26 | 100 | 75 | 75 | 50 |
| 27 | 100 | 75 | 75 | 50 |
| 28 | 100 | 75 | 75 | 50 |
| 29 | 100 | 75 | 75 | 50 |
| 30 | 100 | 75 | 75 | 50 |
| 31 | 100 | 75 | 75 | 50 |
| 32 | 100 | 75 | 75 | 50 |
| 33 | 100 | 75 | 75 | 50 |
| 34 | 100 | 75 | 75 | 50 |
| 35 | 100 | 75 | 75 | 50 |
| 36 | 100 | 75 | 75 | 50 |
| 37 | 100 | 75 | 75 | 50 |
| 38 | 100 | 75 | 75 | 50 |
| 39 | 100 | 75 | 75 | 50 |
| 40 | 100 | 75 | 75 | 50 |
| 41 | 100 | 75 | 75 | 50 |
| 42 | 100 | 75 | 75 | 50 |

*% molded bread out of 4 loaves.

E. Calcium Propionate Antimicrobial Powder

Figure 6:
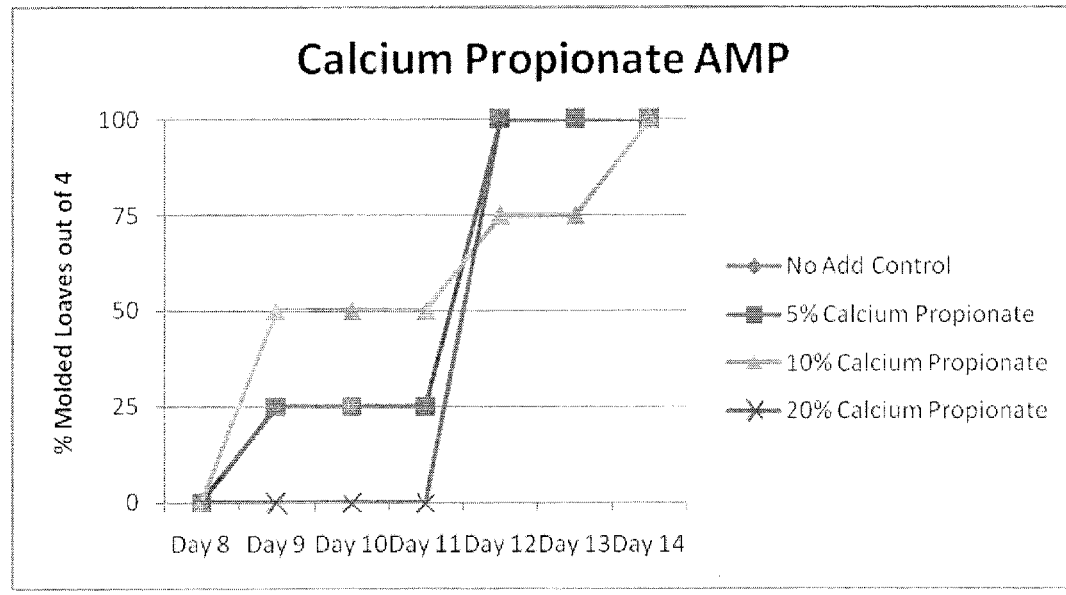
FIG. 6 is a graph of the results from the calcium propionate antimicrobial powder mold inhibition tests from Example 1.

Calcium Propionate Antimicrobial Powder was found to have a slight effect on mold inhibition over the control, but negatively impacted the appearance of the bread. The Calcium Propionate Antimicrobial Powder caused dark spots on the crust. The results are provided in Table 10 below, as well as in FIG. 6.

TABLE 10

Calcium Propionate Antimicrobial Powder.*

| Day | Control | 5% Calcium Propionate | 10% Calcium Propionate | 20% Calcium Propionate |
|---|---|---|---|---|
| 8  | 0   | 0   | 0   | 0   |
| 9  | 25  | 25  | 50  | 0   |
| 10 | 25  | 25  | 50  | 0   |
| 11 | 25  | 25  | 50  | 0   |
| 12 | 100 | 100 | 75  | 100 |
| 13 | 100 | 100 | 75  | 100 |
| 14 | 100 | 100 | 100 | 100 |

*% molded bread out of 4 loaves.

F. Fumaric Acid Antimicrobial Powder

Figure 7:
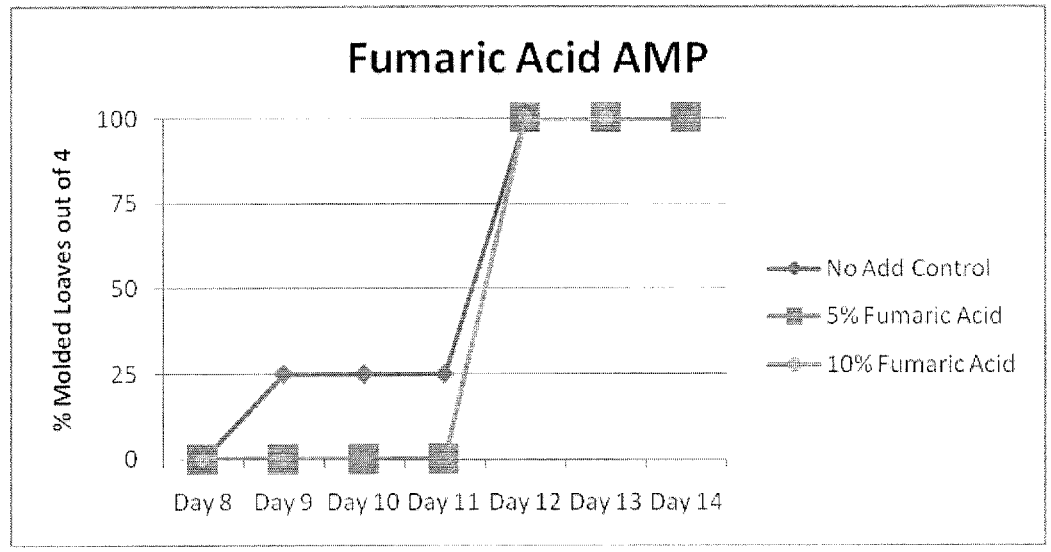
FIG. 7 is a graph of the results from the fumaric acid antimicrobial powder mold inhibition tests from Example 1.

Fumaric Acid Antimicrobial Powder was found to have an effect on inhibiting mold, and it did not impact the appearance of the bread. The results are provided in Table 11 below, as well as in FIG. 7.

TABLE 11

Fumaric Acid Antimicrobial Powder.*

| Day | No Add Control | 5% Fumaric Acid | 10% Fumaric Acid |
|---|---|---|---|
| 8  | 0   | 0   | 0   |
| 9  | 25  | 0   | 0   |
| 10 | 25  | 0   | 0   |
| 11 | 25  | 0   | 0   |
| 12 | 100 | 100 | 100 |
| 13 | 100 | 100 | 100 |
| 14 | 100 | 100 | 100 |

*% molded bread out of 4 loaves.

G. Fermented Carbohydrate Antimicrobial Powder

Figure 8:
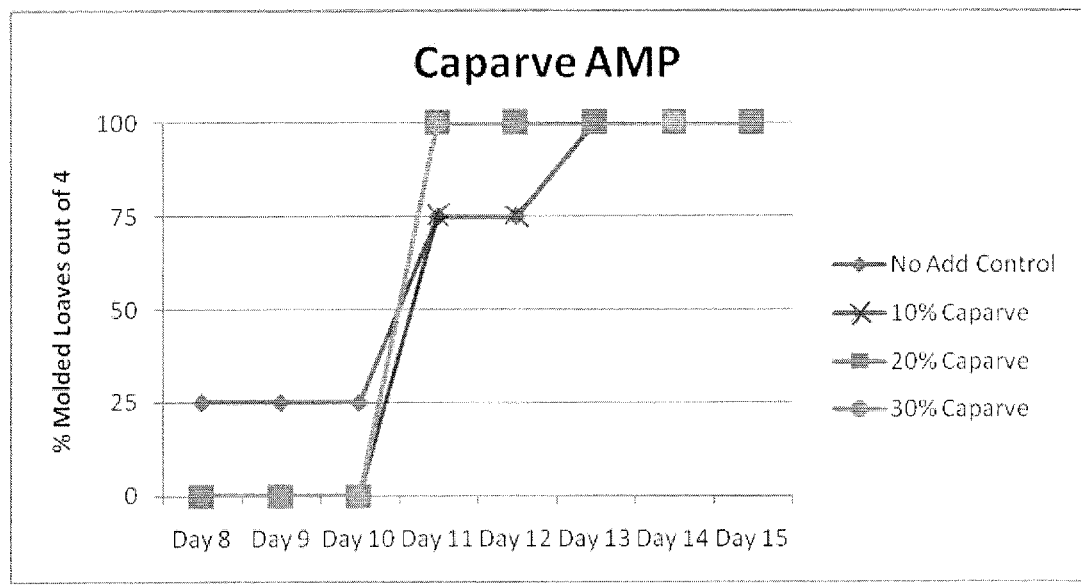
FIG. 8 is a graph of the results from the fermented carbohydrates antimicrobial powder mold inhibition tests from Example 1.

Fermented Carbohydrate Antimicrobial Powder was found to have an effect on mold inhibition over the control, but it negatively impacted the appearance of the bread. This antimicrobial powder caused darkening of the crust color. The results are provided in Table 12 below, as well as in FIG. 8.

TABLE 12

Fermented Carbohydrate Antimicrobial Powder.*

| Day | No Add Control | 10% Caparve | 20% Caparve | 30% Caparve |
|---|---|---|---|---|
| 8  | 25  | 0   | 0   | 0   |
| 9  | 25  | 0   | 0   | 0   |
| 10 | 25  | 0   | 0   | 0   |
| 11 | 75  | 75  | 100 | 100 |
| 12 | 75  | 75  | 100 | 100 |
| 13 | 100 | 100 | 100 | 100 |

*% molded bread out of 4 loaves.

H. Polylysine Antimicrobial Powder

Figure 9:
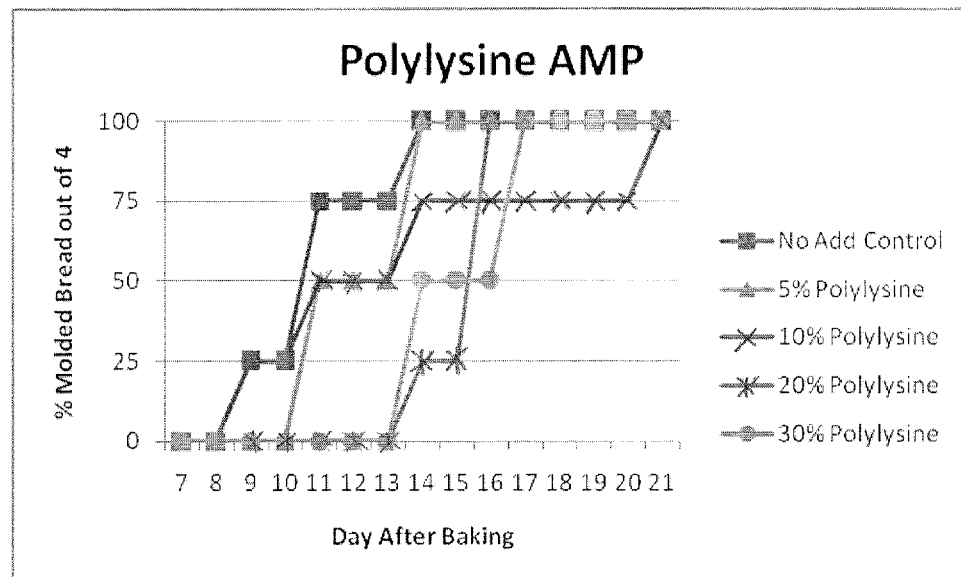
FIG. 9 is a graph of the results from the polylysine antimicrobial powder mold inhibition tests from Example 1.

Polylysine Antimicrobial Powder was effective at mold inhibition over the control, but it negatively impacted the appearance of the bread. This powder caused darkening of the crust color. The results are provided in Table 13 below, as well as in FIG. 9.

TABLE 13

Polylysine Antimicrobial Powder.*

| Day | No Add Control | 5% Polylysine | 10% Polylysine | 20% Polylysine | 30% Polylysine |
|---|---|---|---|---|---|
| 7  | 0   | 0   | 0   | 0   | 0   |
| 8  | 0   | 0   | 0   | 0   | 0   |
| 9  | 25  | 0   | 25  | 0   | 0   |
| 10 | 25  | 0   | 25  | 0   | 0   |
| 11 | 75  | 50  | 50  | 0   | 0   |
| 12 | 75  | 50  | 50  | 0   | 0   |
| 13 | 75  | 50  | 50  | 0   | 0   |
| 14 | 100 | 100 | 75  | 25  | 50  |
| 15 | 100 | 100 | 75  | 25  | 50  |
| 16 | 100 | 100 | 75  | 100 | 50  |
| 17 | 100 | 100 | 75  | 100 | 100 |
| 18 | 100 | 100 | 75  | 100 | 100 |
| 19 | 100 | 100 | 75  | 100 | 100 |
| 20 | 100 | 100 | 75  | 100 | 100 |
| 21 | 100 | 100 | 100 | 100 | 100 |

*% molded bread out of 4 loaves.

I. Cinnamon Antimicrobial Powder

Figure 10:
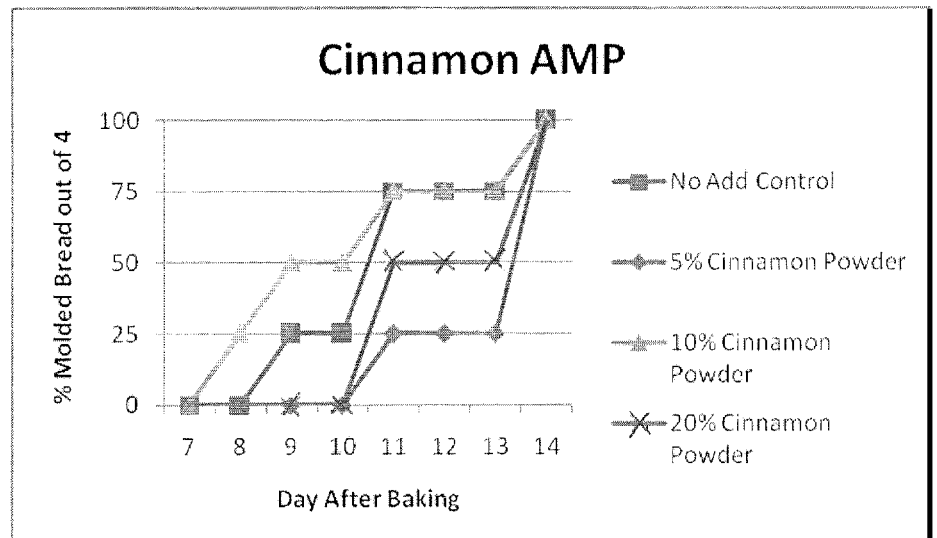
FIG. 10 is a graph of the results from the cinnamon antimicrobial powder mold inhibition tests from Example 1.

Cinnamon Antimicrobial Powder had an effect on mold inhibition over the control, but it negatively impacted the appearance of the bread, as it caused dark specks on the crust. The results are provided in Table 14 below, as well as in FIG. 10.

TABLE 14

Cinnamon Antimicrobial Powder.*

| Day | No Add Control | 5% Cinnamon | 10% Cinnamon | 20% Cinnamon |
|---|---|---|---|---|
| 7  | 0   | 0   | 0   | 0   |
| 8  | 0   | 0   | 25  | 0   |
| 9  | 25  | 0   | 50  | 0   |
| 10 | 25  | 0   | 50  | 0   |
| 11 | 75  | 25  | 75  | 50  |
| 12 | 75  | 25  | 75  | 50  |
| 13 | 75  | 25  | 75  | 50  |
| 14 | 100 | 100 | 100 | 100 |

*% molded bread out of 4 loaves.

J. Sodium Benzoate Antimicrobial Powder

Figure 11:
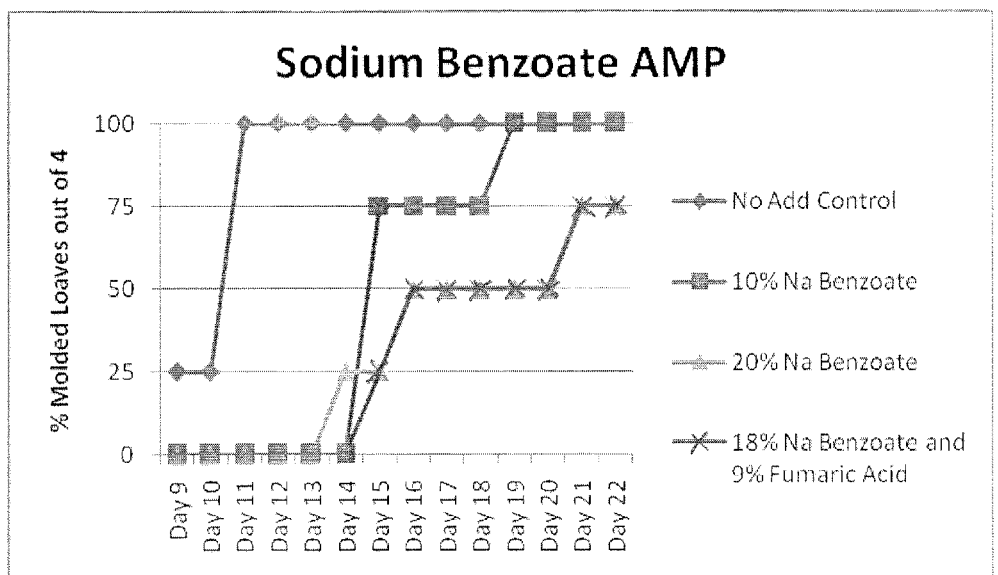
FIG. 11 is a graph of the results from the sodium benzoate antimicrobial powder mold inhibition tests from Example 1.

Sodium Benzoate Antimicrobial Powder was found to be effective at mold inhibition, but it negatively impacted the appearance of the bread by causing a darkening of the crust color. The results are provided in Table 15 below, as well as in FIG. 11.

TABLE 15

Sodium Benzoate Antimicrobial Powder.*

| Day | No Add Control | 10% Na Benzoate | 20% Na Benzoate | 18% Na Benzoate 9% Fumaric Acid |
|---|---|---|---|---|
| 9  | 25  | 0   | 0   | 0   |
| 10 | 25  | 0   | 0   | 0   |
| 11 | 100 | 0   | 0   | 0   |
| 12 | 100 | 0   | 0   | 0   |
| 13 | 100 | 0   | 0   | 0   |
| 14 | 100 | 0   | 25  | 0   |
| 15 | 100 | 75  | 25  | 25  |
| 16 | 100 | 75  | 50  | 50  |
| 17 | 100 | 75  | 50  | 50  |
| 18 | 100 | 75  | 50  | 50  |
| 19 | 100 | 100 | 50  | 50  |
| 20 | 100 | 100 | 50  | 50  |
| 21 | 100 | 100 | 75  | 75  |
| 22 | 100 | 100 | 75  | 75  |

TABLE 15-continued

| | Sodium Benzoate Antimicrobial Powder.* | | | |
|---|---|---|---|---|
| Day | No Add Control | 10% Na Benzoate | 20% Na Benzoate | 18% Na Benzoate 9% Fumaric Acid |
| 23 | 100 | 100 | 75 | 75 |
| 24 | 100 | 100 | 75 | 75 |
| 25 | 100 | 100 | 75 | 75 |
| 26 | 100 | 100 | 75 | 75 |
| 27 | 100 | 100 | 75 | 75 |
| 28 | 100 | 100 | 75 | 75 |
| 29 | 100 | 100 | 75 | 75 |
| 30 | 100 | 100 | 75 | 75 |
| 31 | 100 | 100 | 75 | 75 |
| 32 | 100 | 100 | 75 | 75 |
| 33 | 100 | 100 | 100 | 100 |

*% molded bread out of 4 loaves.

K. Sodium Propionate Antimicrobial Powder

Figure 12:
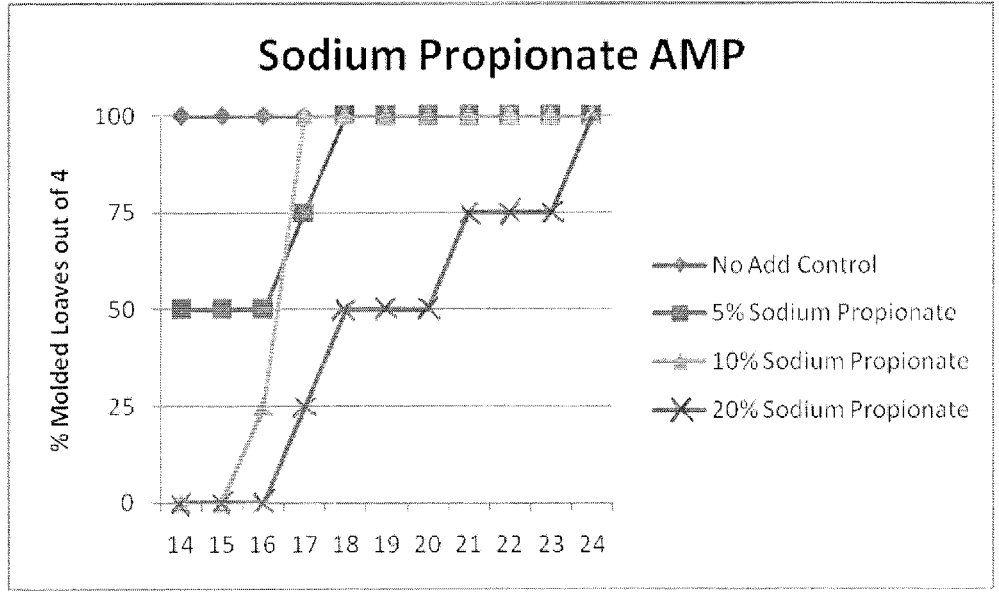
FIG. 12 is a graph of the results from the sodium propionate antimicrobial powder mold inhibition tests from Example 1.

Sodium Propionate Antimicrobial Powder was found to be effective at mold inhibition, but it negatively impacted the appearance of the bread by causing a slight darkening of the crust color. The results are provided in Table 16 below, as well as in FIG. 12.

TABLE 16

| | Sodium Propionate Antimicrobial Powder.* | | | |
|---|---|---|---|---|
| Day | No Add Control | 5% Sodium Propionate | 10% Sodium Propionate | 20% Sodium Propionate |
| 14 | 100 | 50 | 0 | 0 |
| 15 | 100 | 50 | 0 | 0 |
| 16 | 100 | 50 | 25 | 0 |
| 17 | 100 | 75 | 100 | 25 |
| 18 | 100 | 100 | 100 | 50 |
| 19 | 100 | 100 | 100 | 50 |
| 20 | 100 | 100 | 100 | 50 |
| 21 | 100 | 100 | 100 | 75 |
| 22 | 100 | 100 | 100 | 75 |
| 23 | 100 | 100 | 100 | 75 |
| 24 | 100 | 100 | 100 | 100 |

*% molded bread out of 4 loaves.

L. Summary

A summary of the results for each of the Antimicrobial Powders is provided in Table 17 below.

TABLE 17

| | Summary of Results | | |
|---|---|---|---|
| Antimicrobial | Optimum Level[A] | Mold Inhibition | Appearance |
| Sorbic Acid | 10% | Effective | No Impact |
| Natamycin | at least 1.5% | Effective | No Impact |
| Sodium Diacetate | 20% | Moderately Effective | No Impact |
| Potassium Sorbate | at least 10% | Effective | Negative |
| Calcium Propionate | 20% | Slightly Effective | Negative |
| Fumaric Acid | at least 5% | Slightly Effective | No Impact |
| Fermented Carbohydrate | at least 10% | Slightly Effective | Negative |
| Polylysine | at least 10% | Moderately Effective | Negative |
| Cinnamon Powder | at least 5% | Slightly Effective | Negative |
| Sodium Benzoate | at least 10% | Moderately Effective | Negative |
| Sodium Propionate | 20% | Moderately Effective | Negative |

[A]% by weight in powder, based upon the total weight of the Antimicrobial Powder taken as 100% by weight.

Example 2

Dough Formulation B

1. Preparation of Dough

In this Example, hamburger buns containing calcium propionate in the dough were prepared according to the following dough making process, using the ingredients in Table 18 below.

TABLE 18

| Dough Formulation B | | |
|---|---|---|
| INGREDIENTS | Bakers % | Grams |
| White Bread Flour | 100.00 | 1300 |
| Compressed Yeast | 4.00 | 52 |
| Sodium Stearoyl Lactylate (SSL) | .1 | 1.3 |
| Ice Water | 58 | 754 |
| Sugar | 7.00 | 91 |
| Dependox ® AXC[A] | .06 | .78 |
| Calcium Propionate[B] | Variable | Variable |
| Soy Oil | 3 | 39 |
| Salt | 2.3 | 29.9 |

[A]A blend of ascorbic acid, azodicarbonamide (ADA), fungal enzymes, and wheat starch (available from Caravan Ingredients).
[B]Calcium propionate was added at 0%, 0.2% or 0.5% on a flour wt. basis.

All of the ingredients were added to a McDuffy bowl fitted to a Hobart mixer, and mixed on the 1st speed setting (low) for one minute. The sides of the mixing bowl were scraped, and the ingredients were mixed for 15 minutes at the 2nd speed setting (high) until full development. The dough was allowed to rest on a wood bench for 5 minutes, and then divided into 57-gram dough pieces. The dough pieces were rounded, and then allowed to rest for 1 minute. The dough pieces were sheeted slightly, evenly coated with 0.3 grams of sorbic acid powder (described below), and then placed onto glazed bun pans.

Next, the buns were proofed at 104° F. and 86% humidity for 1 hour. The buns were then removed from the proof box and baked at 460° F. for 8 minutes. After baking, the buns were removed from the oven and depanned. They were cooled on wire racks for 30 minutes and then bagged in poly bags with twist ties. The buns were stored at room temperature (~72° F.) to observe mold growth.

2. Antimicrobial Powder

Sorbic Acid Antimicrobial Powders were prepared by mixing all of the ingredients in the table below in a 5 qt Hobart mixer with a paddle attachment for 10 minutes.

| | Grams | | |
|---|---|---|---|
| | 0% | 10% | 20% |
| Sorbic Acid | 0 | 25 | 50 |
| Wheat Flour | 250 | 225 | 200 |
| Total | 250 | 250 | 250 |

3. Results

Figure 13:
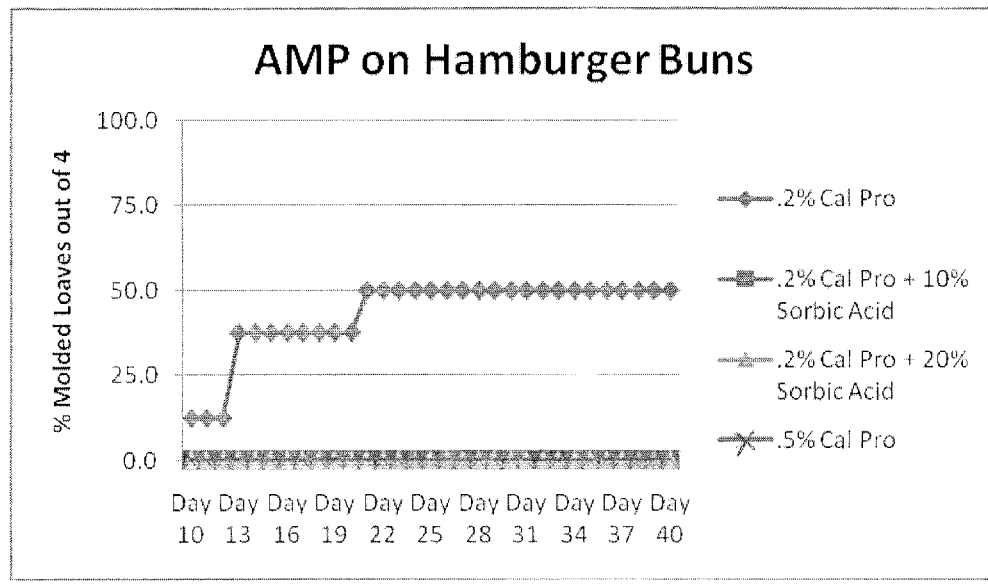
FIG. 13 is a graph of the results from the hamburger bun mold inhibition tests from Example 2 using calcium propionate in the dough and sorbic acid antimicrobial powder.

The 10% Sorbic Acid Antimicrobial Powder with 0.2% calcium propionate added to the dough was found to perform better at inhibiting mold growth than 0.2% calcium propionate alone. The results are provided in Table 19 below, as well as in FIG. 13.

TABLE 19

Sorbic Acid Antimicrobial Powder with Calcium Propionate.*

| Day | 0.5% Calcium Propionate | 0.2% Calcium Propionate | 0.2% Calcium Propionate 10% Sorbic Acid | 0.2% Calcium Propionate 20% Sorbic Acid |
|---|---|---|---|---|
| 10 | 0.0 | 12.5 | 0.0 | 0.0 |
| 11 | 0.0 | 12.5 | 0.0 | 0.0 |
| 12 | 0.0 | 12.5 | 0.0 | 0.0 |
| 13 | 0.0 | 37.5 | 0.0 | 0.0 |
| 14 | 0.0 | 37.5 | 0.0 | 0.0 |
| 15 | 0.0 | 37.5 | 0.0 | 0.0 |
| 16 | 0.0 | 37.5 | 0.0 | 0.0 |
| 17 | 0.0 | 37.5 | 0.0 | 0.0 |
| 18 | 0.0 | 37.5 | 0.0 | 0.0 |
| 19 | 0.0 | 37.5 | 0.0 | 0.0 |
| 20 | 0.0 | 37.5 | 0.0 | 0.0 |
| 21 | 0.0 | 50.0 | 0.0 | 0.0 |
| 22 | 0.0 | 50.0 | 0.0 | 0.0 |
| 23 | 0.0 | 50.0 | 0.0 | 0.0 |
| 24 | 0.0 | 50.0 | 0.0 | 0.0 |
| 25 | 0.0 | 50.0 | 0.0 | 0.0 |
| 26 | 0.0 | 50.0 | 0.0 | 0.0 |
| 27 | 0.0 | 50.0 | 0.0 | 0.0 |
| 28 | 0.0 | 50.0 | 0.0 | 0.0 |
| 29 | 0.0 | 50.0 | 0.0 | 0.0 |
| 30 | 0.0 | 50.0 | 0.0 | 0.0 |
| 31 | 0.0 | 50.0 | 0.0 | 0.0 |
| 32 | 0.0 | 50.0 | 0.0 | 0.0 |
| 33 | 0.0 | 50.0 | 0.0 | 0.0 |
| 34 | 0.0 | 50.0 | 0.0 | 0.0 |
| 35 | 0.0 | 50.0 | 0.0 | 0.0 |
| 36 | 0.0 | 50.0 | 0.0 | 0.0 |
| 37 | 0.0 | 50.0 | 0.0 | 0.0 |
| 38 | 0.0 | 50.0 | 0.0 | 0.0 |
| 39 | 0.0 | 50.0 | 0.0 | 0.0 |
| 40 | 0.0 | 50.0 | 0.0 | 0.0 |

*% of molded buns out of 8 buns (e.g., 50 means 4 out of 8 buns had at least one spot of mold growth).

Example 3

Dough Formulation C

1. Preparation of Dough

In this Example, an all-natural whole wheat bread without calcium propionate was prepared according to the following dough bread making process, using the ingredients in Table 20 below.

TABLE 20

Dough Formulation C

| INGREDIENTS | Bakers % | Grams |
|---|---|---|
| Whole Wheat Flour | 92 | 2760 |
| Compressed Yeast | 5.5 | 165 |
| Vital Wheat Gluten | 8 | 240 |
| Ice Water | 67 | 2010 |
| Sugar | 10 | 300 |
| Strong-Do All Natural Xtra[A] | .25 | 7.5 |
| Soy Oil | 2 | 60 |
| Verdad ™ RV 75[B] | Variable | Variable |
| Salt | 2 | 60 |

[A] A blend of wheat starch, calcium sulfate, enzymes, ascorbic acid, and salt (available from Caravan Ingredients).
[B] PuraQ ™ Verdad ™ RV 75 (a cultured sugar) was added at 0% or 1% on a flour wt. basis.

All of the ingredients except for the salt were added to a 20 qt Hobart mixer, and mixed with a spiral hook on the 1st speed setting (low) for two minutes. The sides of the mixing bowl were scraped, and the ingredients were mixed for 13 minutes at the 2nd speed setting (high). The salt was added, followed by mixing at the 2nd speed setting for an additional 3 minutes until full dough development. The dough was allowed to rest on a wood bench for 10 minutes, and then divided into 535-gram dough pieces, which were then rounded and allowed to rest for an additional 5 minutes. Next, a Gemini Straight Grain Moulder was used, according to the settings in Table 21 below, to sheet and mould the dough pieces.

TABLE 21

Gemini Straight Grain Moulder Settings

| Rollers | 5/3 |
|---|---|
| Pressure Bd. | 32/31 |
| Guide Rails | 16/14 |

The shaped dough pieces were then evenly coated with 2 grams of Natamycin Antimicrobial Powder (described below), and then placed into 1-lb loaf pans. Next, the loaves were proofed at 104° F. and 86% humidity for 1 hour. The loaves were then removed from the proof box and baked at 420° F. for 22 minutes. After baking, the loaves were removed from the oven and depanned. The loaves were cooled on wire racks for 1 hour and then bagged in poly bags with twist ties. The bread was stored at room temperature (~72° F.) to observe mold growth.

2. All Natural Antimicrobial Powder

Natamycin Antimicrobial Powders were prepared by mixing all of the ingredients in the table below in a 5 qt Hobart mixer with a paddle attachment for 10 minutes.

|  | Grams | |
|---|---|---|
|  | 0% | 1.5% |
| Natamycin | 0 | 3.75 |
| Wheat Flour | 250 | 246.25 |
| Total | 250 | 250 |

3. Results

Figure 14:
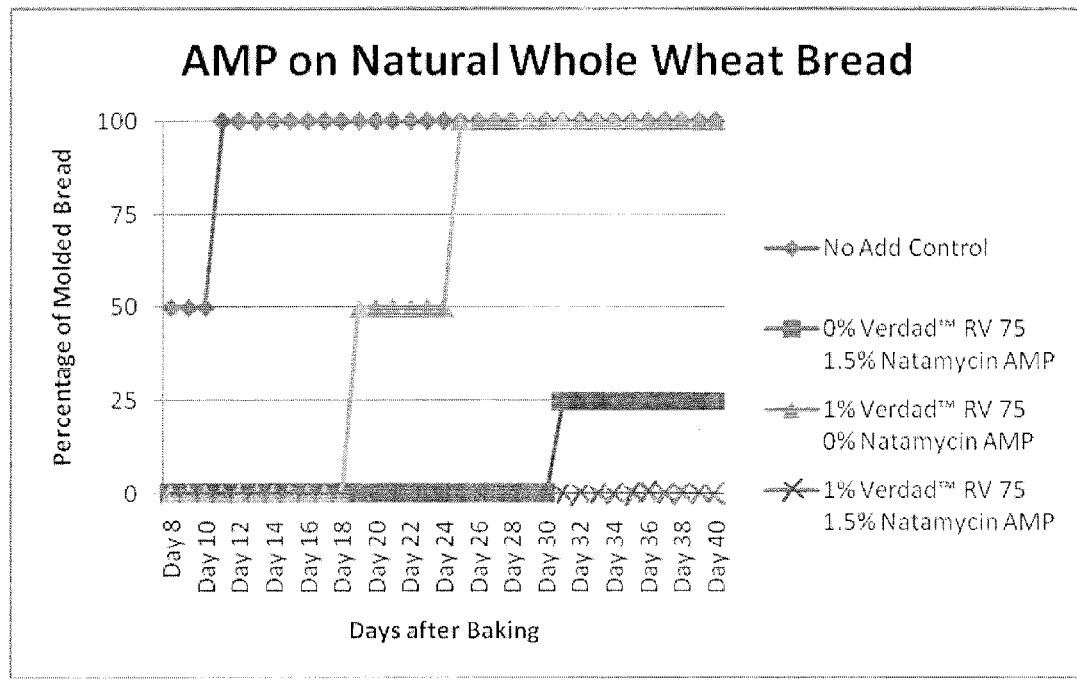
FIG. 14 is a graph of the results from the whole wheat bread mold inhibition tests from Example 3 using a natural preservative in the dough and natamycin antimicrobial powder.

The combination of 1.5% Natamycin Antimicrobial Powder and 1% Verdad™ RV75 in the dough performed very well at inhibiting mold growth. The results are provided in Table 22 below, as well as in FIG. 14.

TABLE 22

Natamycin Antimicrobial Powder and Verdad ™ RV75.*

| Day | No Add Control | 0% Verdad ™ RV 75 1.5% Natamycin AMP | 1% Verdad ™ RV 75 0% Natamycin AMP | 1% Verdad ™ RV 75 1.5% Natamycin AMP |
|---|---|---|---|---|
| 8 | 50 | 0 | 0 | 0 |
| 9 | 50 | 0 | 0 | 0 |
| 10 | 50 | 0 | 0 | 0 |
| 11 | 100 | 0 | 0 | 0 |
| 12 | 100 | 0 | 0 | 0 |
| 13 | 100 | 0 | 0 | 0 |
| 14 | 100 | 0 | 0 | 0 |
| 15 | 100 | 0 | 0 | 0 |
| 16 | 100 | 0 | 0 | 0 |
| 17 | 100 | 0 | 0 | 0 |
| 18 | 100 | 0 | 0 | 0 |
| 19 | 100 | 0 | 50 | 0 |
| 20 | 100 | 0 | 50 | 0 |
| 21 | 100 | 0 | 50 | 0 |
| 22 | 100 | 0 | 50 | 0 |
| 23 | 100 | 0 | 50 | 0 |
| 24 | 100 | 0 | 50 | 0 |

TABLE 22-continued

Natamycin Antimicrobial Powder and Verdad ™ RV75.*

| Day | No Add Control | 0% Verdad ™ RV 75 1.5% Natamycin AMP | 1% Verdad ™ RV 75 0% Natamycin AMP | 1% Verdad ™ RV 75 1.5% Natamycin AMP |
|---|---|---|---|---|
| 25 | 100 | 0 | 100 | 0 |
| 26 | 100 | 0 | 100 | 0 |
| 27 | 100 | 0 | 100 | 0 |
| 28 | 100 | 0 | 100 | 0 |
| 29 | 100 | 0 | 100 | 0 |
| 30 | 100 | 0 | 100 | 0 |
| 31 | 100 | 25 | 100 | 0 |
| 32 | 100 | 25 | 100 | 0 |
| 33 | 100 | 25 | 100 | 0 |
| 34 | 100 | 25 | 100 | 0 |
| 35 | 100 | 25 | 100 | 0 |
| 36 | 100 | 25 | 100 | 0 |
| 37 | 100 | 25 | 100 | 0 |
| 38 | 100 | 25 | 100 | 0 |
| 39 | 100 | 25 | 100 | 0 |
| 40 | 100 | 25 | 100 | 0 |

*% of molded bread out of 4 loaves.

Example 4

Crust Analysis

Sorbic Acid Antimicrobial Powder

In this Example, three conventional bread doughs were prepared for this experiment. Two doughs contained 0% sorbic acid and one dough contained 0.1% sorbic acid. One of the doughs with 0% sorbic acid was treated with a 10% Sorbic Acid Antimicrobial Powder as described in Example 1, before being placed in the pan. Two loaves from each dough were analyzed for sorbic acid content in the bread crumb and the bread crust. The results are below.

| Crust Analysis Results | | Sample | Sorbic Acid on Dry Basis (ppm) |
|---|---|---|---|
| No Add Control | | Crumb | <100 |
| | | Crust | <100 |
| 10% Sorbic Acid Powder | Loaf 1 | Crumb | <100 |
| | | Crust | 849 |
| 0% Sorbic Acid in Dough | Loaf 2 | Crumb | <100 |
| | | Crust | 829 |
| 0.1% Sorbic Acid in Dough | Loaf 1 | Crumb | 856 |
| | | Crust | 451 |
| | Loaf 2 | Crumb | 863 |
| | | Crust | 440 |

The results conclusively show a significant amount of sorbic acid on the crust is attributable to the Antimicrobial Powder.

We claim:

1. A method of extending the shelf-life of a dough-based product comprising:
   treating the exterior surface of a dough with an antimicrobial powder to yield a treated dough having said antimicrobial powder on the exterior surface thereof, said antimicrobial powder comprising an antimicrobial agent dispersed in a carrier powder selected from the group consisting of flours, calcium sulfate, silica, starches, fibers, and combinations thereof, wherein said antimicrobial agent is selected from the group consisting of sorbic acid, natamycin, sodium diacetate, calcium propionate, sodium propionate, potassium sorbate, fumaric acid, polylysine, sodium benzoate, fermented carbohydrates, and combinations thereof, wherein said antimicrobial powder comprises:
   less than 2% by weight salt;
   less than about 1% by weight fat or oil; and
   a moisture content of less than about 20% by weight, based upon the total weight of the antimicrobial powder taken as 100% by weight; and
   baking said treated dough having said antimicrobial powder on the exterior surface thereof to yield said dough-based product having a mold-free shelf-life of at least about 7 days under ambient conditions.

2. The method of claim 1, further comprising shaping said dough prior to said treating.

3. The method of claim 1, further comprising proofing said treated dough prior to said baking.

4. The method of claim 1, wherein said treating comprises coating said exterior surface of said dough with a layer of said antimicrobial powder.

5. The method of claim 4, wherein at least about 75% of the exterior surface area of said dough is coated with said antimicrobial powder.

6. The method of claim 1, wherein said baking comprises baking said dough in or on a baking pan.

7. The method of claim 6, wherein said exterior surface of said dough is treated with said antimicrobial powder prior to placing said dough in or on said baking pan.

8. The method of claim 6, further comprising proofing said dough after placing said dough in or on said baking pan.

9. The method of claim 1, wherein said antimicrobial powder is substantially salt-free.

10. The method of claim 1, wherein the amount of said antimicrobial agent is selected from the group consisting of from about 5% to about 20% sorbic acid, from about 0.5% to about 5% natamycin, from about 10% to about 20% sodium diacetate, from about 5% to about 30% calcium propionate, from about 5% to about 30% sodium propionate, from about 5% to about 30% potassium sorbate, from about 5% to about 30% fumaric acid, from about 0.5% to about 40% polylysine, from about 10% to about 30% sodium benzoate, from about 5% to about 30% fermented carbohydrates, and combinations thereof, based on the total weight of the antimicrobial powder taken as 100%.

11. The method of claim 1, wherein the amount of said antimicrobial agent is selected from the group consisting of from about 7% to about 10% sorbic acid, from about 1.5% to about 5% natamycin, from about 10% to about 20% sodium diacetate, from about 5% to about 20% calcium propionate, from about 10% to about 20% sodium propionate, from about 10% to about 20% potassium sorbate, from about 10% to about 15% fumaric acid, from about 5% to about 30% polylysine, from about 15% to about 25% sodium benzoate, from about 10% to about 30% fermented carbohydrates, and combinations thereof, based on the total weight of the antimicrobial powder taken as 100%.

12. A method of extending the shelf-life of a dough-based product comprising:
   shaping a dough;
   treating the exterior surface of a dough with an antimicrobial powder to yield a treated dough having said antimicrobial powder on the exterior surface thereof, said antimicrobial powder comprising an antimicrobial agent dispersed in a carrier powder selected from the group consisting of flours, calcium sulfate, silica, starches, fibers, and combinations thereof, wherein said antimicrobial agent is selected from the group consisting of sorbic acid, natamycin, sodium diacetate, calcium propionate, sodium propionate, potassium sorbate, fumaric acid, polylysine, sodium benzoate, fermented carbohydrates, and combinations thereof, and wherein said antimicrobial powder comprises:
less than about 1% by weight fat or oil; and
a moisture content of less than about 20% by weight, based upon the total weight of the antimicrobial powder taken as 100% by weight;
proofing said treated dough having said antimicrobial powder on the exterior surface thereof; and
baking said treated dough having said antimicrobial powder on the exterior surface thereof to yield said dough-based product having a mold-free shelf-life of at least about 7 days under ambient conditions.

13. The method of claim 12, wherein said antimicrobial powder is substantially salt-free.

14. The method of claim 12, wherein said antimicrobial powder is free of calcium propionate, sodium propionate, potassium sorbate, sodium diacetate, ascorbic acid, and propionic acid.

15. The method of claim 12, wherein said dough comprises anti-staling enzymes selected from the group consisting of maltogenic exoamylase, G4 amylase, G+ amylase, and combinations thereof to extend both the mold-free shelf life and non-staling shelf life of the dough-based product, as compared to a dough-based product without said antimicrobial powder and anti-staling enzymes.

16. The method of claim 12, wherein the amount of said antimicrobial agent is selected from the group consisting of from about 5% to about 20% sorbic acid, from about 0.5% to about 5% natamycin, from about 10% to about 20% sodium diacetate, from about 5% to about 30% calcium propionate, from about 5% to about 30% sodium propionate, from about 5% to about 30% potassium sorbate, from about 5% to about 30% fumaric acid, from about 0.5% to about 40% polylysine, from about 10% to about 30% sodium benzoate, from about 5% to about 30% fermented carbohydrates, and combinations thereof, based on the total weight of the antimicrobial powder taken as 100%.

17. The method of claim 12, wherein the amount of said antimicrobial agent is selected from the group consisting of from about 7% to about 10% sorbic acid, from about 1.5% to about 5% natamycin, from about 10% to about 20% sodium diacetate, from about 5% to about 20% calcium propionate, from about 10% to about 20% sodium propionate, from about 10% to about 20% potassium sorbate, from about 10% to about 15% fumaric acid, from about 5% to about 30% polylysine, from about 15% to about 25% sodium benzoate, from about 10% to about 30% fermented carbohydrates, and combinations thereof, based on the total weight of the antimicrobial powder taken as 100%.

* * * * *